United States Patent [19]

Rolfe et al.

[11] Patent Number: 5,141,745
[45] Date of Patent: Aug. 25, 1992

[54] NODULATION INDUCING FACTORS

[75] Inventors: Barry G. Rolfe, Curtin; John W. Redmond, West Ryde; Michael Batley, Sydney; Michael A. Djordjevic, Aranda, all of Australia

[73] Assignee: The Lubrizol Corporation, Wickliffe, Ohio

[21] Appl. No.: 393,050

[22] Filed: Aug. 8, 1989

Related U.S. Application Data

[63] Continuation of Ser. No. 844,870, Mar. 27, 1986, abandoned.

[51] Int. Cl.$^5$ .................. A01N 63/00; A01N 43/00; C12R 1/41; C05F 11/08; A01C 1/06
[52] U.S. Cl. .......................... 424/93 D; 435/252.2; 435/878; 71/7; 71/88; 47/57.6; 47/DIG. 9; 47/DIG. 10
[58] Field of Search ............ 71/7, 88; 47/58, DIG. 9, 47/DIG. 10, 57.6; 435/252.2, 878; 424/93

[56] References Cited

U.S. PATENT DOCUMENTS 2,681,907  6/1954  Wender .................. 260/210
4,644,011  2/1987  Ballenegger et al. ......... 514/456

FOREIGN PATENT DOCUMENTS 2228434  9/1974  France .
55-64508  10/1980  Japan .

OTHER PUBLICATIONS

Firmin et al. 1986, Nature 324:90-92.
Spaink et al. 1987, Nature 328:337-340.
Bhuvaneswari et al., Plant Physiol. (1977) 60:486-491.
Rolfe, Barry G., BioFactors (1988) 1(1):3-10.
Zaat et al., Journal of Bacteriology (Jan. 1987) pp. 198-204.
Djordjevic et al., The EMBO Journal (1987) 6(5):1173-1179.
Peters et al., Science (Aug. 1986) 233:977-980.
Bolton et al., Science (May 1986) 232:983-985.
Stachel et al. (Dec. 1985) Nature 318:624-629.
Chem. Abstracts 82(17):143, abstract no. 107545b (1975). Kato et al.
Chem. Abstracts 84(3):133, abstract No. 13498c (1976). Honma et al.
Chemical Abstracts 93(11):255, abstract no. 109004a (1980), Jpn. Kokai Tokyo Koho.
Chemical Abstracts 103(4):310, ref. no. 27298k (1985), Jpn. Kokai Tokyo Koho.
Rossen et al. (1985) EMBO J. 4:3369-3373.
Chemical Abstracts 70:70, ref. no. 112355w (1969).
Innes et al. (1985) Mol. Gen. Genet. 201:426-432.
Rolfe et al. (1985) *Nitrogen Fixation Research Progress* Evans et al. (eds.) Martinus Nijhoff, Dordrecht, The Netherlands, pp. 79-85.
Scott et al. (1985) ibid. p. 130.
Schofield et al. ibid. p. 125.
Mulligan and Long (1985) Proc. Natl. Acad. Sci. USA 82:6609-6613.
Kondorosi et al. (1985) *Nitrogen Fixation Research Progress* Evans et al. eds. Martinus Nijhoff, Dordrecht, The Netherlands, pp. 73-75.
Thorton (1929) Proc. Royal Soc. B 164:481.
Valera and Alexander (1965) J. Bacteriol. 89:1134-1139.
Peters and Alexander (1966) Soil Science 102:380-387.
Turner (1955) Annals Botany 19:149-160.
Nutman (1953) Annals Botany 17:95-126.
Baghwat and Thomas (1982) Applied Environ. Microbiol. 43:800-805.
Halverson and Stacey (1984) Plant Physiol. 74:84-89.
Halverson and Stacey (1985) Plant Physiol. 77:621-624.
Molina and Alexander (1967) Can. J. Microbiol. 13:819-827.
Weir (1960) Phyton 15:109-118.
Sherman et al. (1986) EMBO J. 5:647-652.

*Primary Examiner*—David T. Fox
*Attorney, Agent, or Firm*—Greenlee and Associates

[57] ABSTRACT

Nodulation gene-inducing factors have been isolated and identified. A number of substituted flavones, some of which are components of exudates and extracts of leguminous plants, have been found to induce expression of certain nodulation genes in Rhizobium strains. Three components of clover extract 7,4'-dihydroxyflavone, 7,4'-dihydroxy-3'methoxyflavone, and 4'-hydroxy-7-methoxyflavone have been identified as nodulation inducers of certain *Rhizobium trifolii* nod genes. A number of other flavonoids including flavones, flavanones, flavanols and dihydroflavanols, not necessarily found in legume exudates, were also found to induce expression of certain nodulation genes.

40 Claims, 2 Drawing Sheets

NODULATION INDUCING FACTORS

This application is a continuation, of application Ser. No. 06/844,870, filed Mar. 27, 1986, now abandoned.

FIELD OF THE INVENTION

The present invention relates in general to the field of legume-Rhizobium symbiosis and in particular to the identification of flavonoid compounds which stimulate expression of rhizobia nodulation genes and elicit faster rates of legume nodulation by rhizobia. These compounds are useful in general for selective control of gene expression and in particular in improved legume inoculating compositions.

BACKGROUND OF THE INVENTION

Soil bacteria of the genus Rhizobium, a member of the family Rhizobiaceae, are capable of infecting plants and inducing highly differentiated structures, root nodules, within which atmospheric nitrogen is reduced to ammonia by the bacteria. The host plant, most often of the family Leguminosa, utilizes the ammonia as a source of nitrogen. Previously, Rhizobium species were classified in two groups, either as fast-growing or slow-growing. The group of slow-growing rhizobia has recently been reclassified as a new genus designated Bradyrhizobium (Jordan, D.C. (1982) Int. J. Syst. Bacteriol. 32:136). Included in the classification of fast-growing rhizobia are *R. trifolii*, which nodulate clover, *R. melitoti*, which nodulate alfalfa, *R. leguminosarum*, which nodulate pea, and *R. phaseolus*, which nodulate bean. These fast-growing strains of rhizobia generally display narrow host range. The fast-growing *R. japonicum* strains which nodulate Glycine max cv. Peking and fast-growing members of the cowpea Rhizobium display broader host range. The Bradyrhizobium, slow-growing rhizobia, include the commercially important soybean nodulating strains *B. japonicum* (i.e., strains USDA 110 and 123), the slow-growing promiscuous rhizobia of the cowpea group, and *B. parasponia* (formerly Parasponia Rhizobium) which nodulates the non-legume Parasponia, as well as a number of tropical legumes including cowpea and siratro.

Nodulation and the development of effective symbiosis is a complex process requiring both bacterial and plant genes. Several recent reviews of the genetics of the Rhizobium-legume interaction are found in Broughton, W. J., ed. (1982) *Nitrogen Fixation*, Volumes 2 and 3 (Clarendon Press, Oxford); Puhler, A. ed. (1983) *Molecular Genetics of the Bacteria-Plant Interaction* (Springer-Verlag, Berlin); Szalay, A. A. and Leglocki, R. P., eds. (1985) *Advances in Molecular Genetics of the Bacteria-Plant Interaction* Cornell University Publishers, Ithaca, N.Y.; Long, S. R. (1984) in *Plant Microbe Interactions* Volume 1, Kosuge, T. and Nester, E. W., eds. (MacMillan, N.Y.) pp. 265–306; and Verma, D. P. S. and Long, S. L. (1983) International Review of Cytology (Suppl. 14), Jeon, K. W. (ed.), Academic Press, p. 211–245.

In fast-growing species genes required for nodulation and nitrogen fixation are located on large Sym plasmids. Although the process of recognition, infection and nodule development is complex, it appears that at least for the fast-growing rhizobia relatively few bacterial genes are directly involved, and these are closely linked on the Sym plasmid. For example, a 14 kb fragment of the *R. trifolii* Sym plasmid is sufficient to confer clover-specific nodulation upon a Rhizobium strain cured of its Sym plasmid (Schofield et al. (1984) Plant Mol. Biol. 3:3–11). Nodulation and nitrogenase genes are localized on symbiotic plasmids in R. leguminosarum (Downie et al (1983) Mol. Gen. Genet. 190:359–365) and in *R. meliloti* (Kondorosi et al. (1984) Mol. Gen. Genet. 193:445–452). In contrast, no Sym plasmids have been associated with the slow-growing rhizobia, *B. japonicum* or *B. parasponia*. The nitrogenase and nodulation genes of these organisms are believed to be encoded on the chromosome.

Fine structure genetic mapping has been used to locate individual nodulation genes in both fast- and slow-growing rhizobia. Transposon mutagenesis, most often using the transposon Tn5, has identified about 10 nodulation genes associated with non-nodulation and delayed nodulation phenotypes (Djordjevic et al. (1985) Mol. Gen. Genet. 200:263–271; Downie et al. (1985) Mol. Gen. Genet. 198:255–262; Kondorosi et al., 1984 and Innes et al. (1985) Mol. Gen. Genet. 201:426–432). Common nodulation genes designated nodABC and D, which are functionally and structurally conserved among the fast-growing rhizobia, have been identified by hybridization studies and cross-species complementation experiments. Both *B. parasponia* (Marvel et al. (1985) Proc. Natl. Acad. Sci. USA 82:5841–5845) and *B. japonicum* (Russel et al. (1985) J. Bacteriol. 164:1301–1308) contain nodulation genes which can functionally complement mutations in fast-growing rhizobia and which show strong structural homology to nodulation gene regions of *R. meliloti* and *R. leguminosarum*. Recent work (Rolfe et al. (1985) *Nitrogen Fixation Research Progress*, Evans et al. (eds.) Martinus Nijhoff, Dordrecht, The Netherlands, p. 79–85; Scott et al. (1985) ibid., p. 130; and Schofield et al. (1985) ibid., p. 125) reports that the structure, organization and regulation of the common nod genes is conserved in both fast- and slow-growing rhizobia. Structural and functional conservation extends to other nodulation genes (nodE, F, I and J) (Djordjevic et al., (1985) Plant Mol. Biol. 4:147–160).

In the common nod region, nodA, B and C genes are grouped sequentially and are likely to be coordinately transcribed as a single transcriptional unit. The nodD gene is transcribed divergently from the nodABC operon (Egelhoff et al. (1985) DNA 4:241–248; Jacobs et al. (1985) J. Bacteriol. 162:469–476; Rossen et al. (1984) Nucl. Acids Res. 12:9497–9508; and Torok et al. (1984) Nucl. Acids Res. 12:9509–9524). Divergent promoters for the nodABC operon and nodD are presumably located in the region between nodD and nodA. In *R. trifolii*, at least (see FIG. 1), nodI and nodJ are believed to be cotranscribed with nodABC, as a nodABC(IJ) operon while nodE and F form a nodEF operon. Both nodG and nodH are believed to be transcribed independently.

The manner in which the nodulation genes are regulated is also conserved among Rhizobium and Bradyrhizobium strains. Only one of the nodulation genes, nodD, is constitutively expressed in free-living rhizobia. Expression of the other identified nodulation genes including nodABCEFGHI and J requires the presence of legume exudate and the gene product of nodD (Mulligan and Long (1985) Proc. Natl. Acad. Sci. USA 82:6609–6613; Rossen et al. (1985) EMBO J. 4:3369–3373; Innes et al., 1985). Conserved DNA sequence elements are found within the promoter regions of the nodABC(IJ) operon in *R. trifolii, R. meliloti, R.*

*leguminosarum* and *B. parasponia*, and in the nodEF operon and nodH in *R. trifolii*. (Scott et al. (1985); Rolfe et al. (1985); Kondorosi et al. (1985) *Nitrogen Fixation Research Progress*, Evans et al. (eds.) Martinus Nijhoff, Dordrecht, The Netherlands, p. 73-75). These consensus sequences are associated with exudate-inducible expression of the nod genes and their presence in various rhizobia suggest a conserved regulatory mechanism.

Sym plasmid encoded nodulation genes of Rhizobium strains and their analogues in Bradyrhizobium strains affect the early stages of nodule formation including host-bacterium recognition, infection and nodule development. Individual wild type strains of Rhizobium and Bradyrhizobium species display some variation in these early nodulation steps. This variation is reflected in differences in relative rates of initiation of nodulation and ultimately in differences in competitiveness between strains for nodule occupancy. Strains which initiate infection and nodules earlier will occupy a greater portion of the nodules on a given plant. Improving the competitiveness of a specific Rhizobium is an important part of the development of improved inocula for legumes. A more effective Rhizobium strain, which would likely constitute an improved inoculum, must be able to out-compete the indigenous rhizobia population for nodule occupancy in order for their improved qualities to impact on the inoculated legume. An inoculating composition or an inoculating method which would improve competitiveness of a selected inoculant strain is therefore of significant commercial importance.

The establishment of nitrogen-fixing nodules is a multistage process involving coordinated morphological changes in both bacterium and plant requiring precise regulation of plant and Rhizobium genes. It has been suggested that an exchange of signals between plant and bacterium is requisite for mutual recognition and coordination of the steps of infection and nodulation development (Nutman, P. S. (1965) in *Ecology of Soil Borne Pathogens*, eds. F. K. Baker and W. C. Snyder, University of California Press, Berkeley, pp. 231-247; Bauer, W. D. (1981) Ann. Rev. Plant Phys. 32:407-449; and Schmidt, E. E. (1979) Ann. Rev. Microbiol. 33:355-376). The regulation of nodulation genes of rhizobia by chemical factors excreted by legumes in exudates is a specific demonstration of communication between host and symbiont.

Legume exudates have been previously linked to both stimulation (Thornton (1929) Proc. Royal Soc. B 164:481; Valera and Alexander (1965) J. Bacteriol. 89:1134-1139; Peters and Alexander (1966) Soil Science 102:380-387) and inhibition (Turner (1955) Annals Botany 19:149-160; and Nutman (1953) Annals Botany 17:95-126) of nodulation by rhizobia.

Turner (1955) reported that addition of activated charcoal to rooting medium of clover plants led to an increased rate of nodule initiation. Activated charcoal was demonstrated to remove by adsorption an unidentified inhibitory substance secreted by clover roots. Nutman (1953) reported that clover roots excreted a substance inhibitory to nodulation. The substance was not identified but was found to be associated with the stage of nodulation on the plant. In both cases, it was suggested that both stimulatory and inhibitory factors were present in the root exudate.

Valera and Alexander (1965) and Peters and Alexander (1966) reported a nodulation enhancing factor in legume exudates that was dialyzable, water soluble and thermostable. This factor was replaceable by coconut water. More recently, Baghwat and Thomas (1982) Applied Environ. Microbiol. 43:800-805 described a stimulatory factor from legume exudates that was thermostable, was high molecular weight (about $2 \times 10^5$) and was composed of protein and neutral hexoses. This factor was associated with elimination of nodulation delay in a certain cowpea Rhizobium strain. Halverson and Stacey (1984) Plant Physiol. 74:84-89; and (1985) Plant Physiol. 77:621-624 reported an exudate factor having a similar effect on nodulation initiation in *B. japonicum* USDA 110 mutants. In contrast to Baghwat and Thomas (1982), this stimulator of nodulation is described as a heat and trypsin sensitive protein, a galactose-specific lectin.

In addition to factors present in legume exudate, diverse chemicals have been identified as stimulators or inhibitors of nodulation. Reported stimulators of nodulation include inositol, indole, 2-phenol-n-butyric acid, D-leucine, barbituric acid, pyridine-3-sulfonate and quercetin (Molina and Alexander (1967) Can. J. Microbiol. 13:819-827; and Weir (1960) Phyton 15:109-118).

SUMMARY OF THE INVENTION

The present work describes the isolation and identification of substituted flavones which are nodulation gene-inducing factors. Exudates and extracts of a number of leguminous plants contain chemical factors which induce expression of certain nodulation genes (nodABCEFGHI and J). Nod gene fusions to an *E. coli* lacZ gene which encodes β-galactosidase activity have been constructed to study the regulation of nodulation genes. The construction of these gene fusions employed the transposon MudI1734 (containing a promoterless lacZ gene) and is described Innes et al. (1985). In these genetic constructions lacZ expression, as β-galactosidase activity, reflects expression of the nodulation gene into which MudI1734 is inserted. Strains of *R. trifolii* containing MudI1734 in the correct orientation with respect to a nodulation gene express β-galactosidase on induction of that nod gene. So in combination with well known methods for assaying β-galactosidase activity, these strains constitute an assay system for induction of nodulation genes. The β-galactosidase assays have been used to demonstrate the presence of chemical factors which stimulate nodulation genes in exudates of several legumes including clover, alfalfa, pea, bean, soybean, lupine, siratro and desmodium (Table 1). Nodulation gene-inducing factors are not detected in exudates of non-legumes.

Three components of clover extract have been isolated and identified as stimulators of nodulation gene induction. All of these components, 7,4'-dihydroxyflavone, 7,4'-dihydroxy-3'-methoxyflavone, and 4'-hydroxy-7-methoxyflavone are substituted flavones.

By employing the nodulation gene induction assay, a number of chemicals structurally related to the flavones identified in clover extract have been assayed for activity. A structurally related class of molecules has been defined which is associated with nodulation gene induction, all of which are substituted flavones including flavanones, flavanols (3-hydroxyflavones) and dihydroflavanols (3-hydroxydihydroflavones).

In addition to the direct stimulation of nod genes, these substituted flavones also elicit faster initiation of nodulation by certain strains of rhizobia. A split-root nodulation assay for this activity is provided. A strain which initiates nodulation faster than other infective strains will attain higher nodule occupancy and therefore be more competitive.

It is a principal object of this invention to identify a structurally related class of molecules, substituted flavones, which stimulate nodulation gene expression and elicit faster initiation of nodulation.

It is another object of this invention to describe the use of these stimulatory substances as components of nodulation inducing compositions and legume inoculating compositions. Inducing compositions contain as an essential ingredient an effective amount of a nodulation gene-inducing factor comprising a substituted flavone. Legume inoculating compositions contain as essential ingredients a strain of rhizobium capable of nodulating the legume and an effective concentration of a nodulation gene-inducing factor. The inoculant rhizobia combined with or in such compositions will be more competitive for infection and nodulation compared to bacterial populations not exposed to the factor.

It is another object of this invention to provide a method of inoculating legumes employing nodulation inducing or legume inoculating compositions of the present invention.

It is a further object of this invention to provide a method of selectively expressing, in a bacterium, a gene which contains a legume exudate-inducible promoter and a structural gene under its control by contacting the bacterium with an effective concentration of a nodulation gene-inducing factor. Legume exudate controlled expression of nod genes has been demonstrated not only in Rhizobium strains, but also in Agrobacterium strains.

It is another object of this invention to provide a method of preparing extracts of leguminous plants which are active for induction of nod gene expression and eliciting faster initiation of nodulation. Active extracts are obtained by extraction of legume seedlings with aqueous ethanol, followed by chromatographic separation of the components of the extract. These procedures remove nodulation inhibitory substances that have been identified as components in legume exudate. Individual components of the exudate are then assayed for nodulation gene induction and/or stimulation of faster initiation of nodulation.

Additional objects and advantages of this invention will be apparent from the following description.

DETAILED DESCRIPTION OF THE INVENTION

Figure 1:
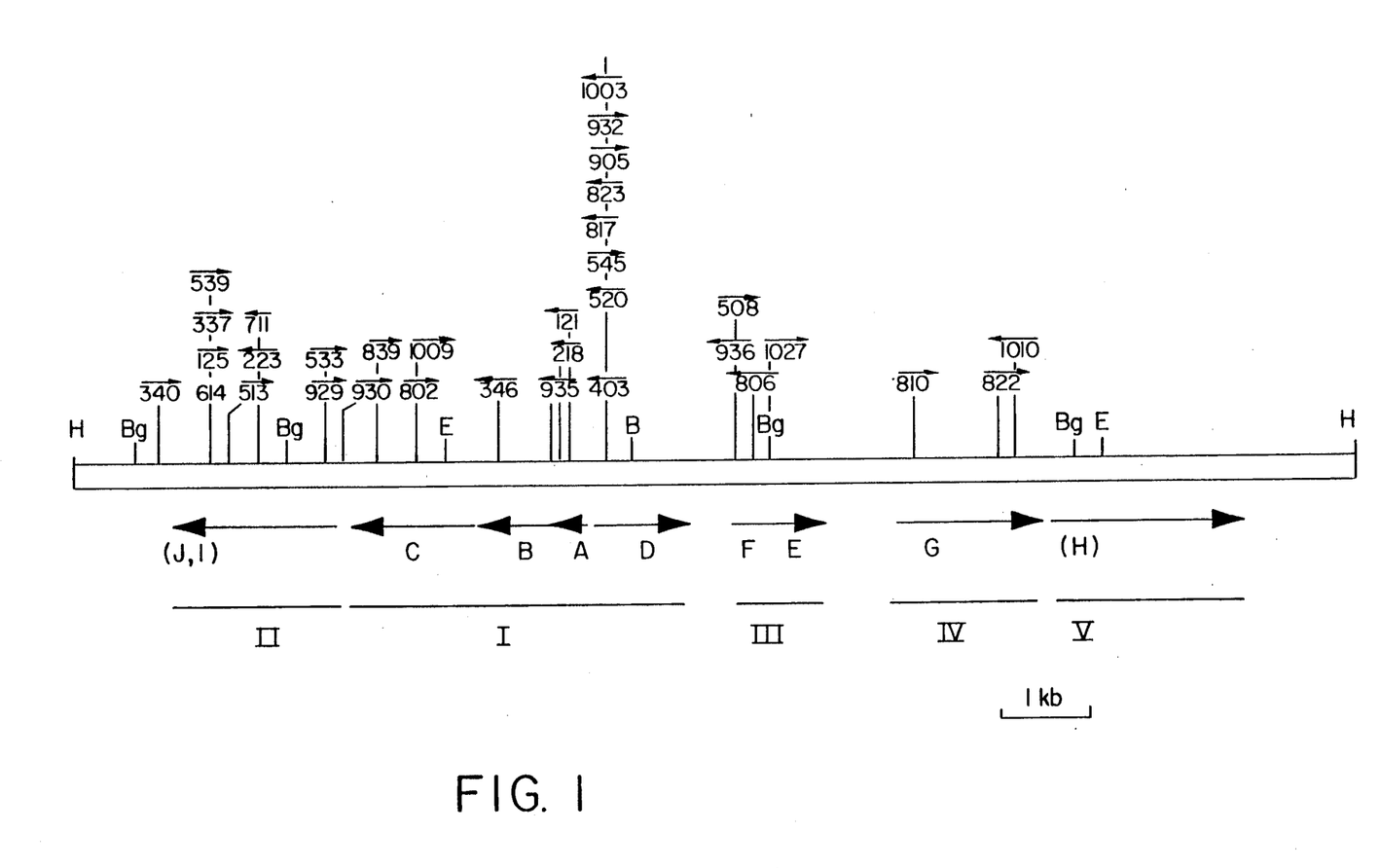
FIG. 1 is a diagram giving the locations of MudI1734 (kan, lac) insertions in the 14kb HindIII DNA fragment of the *R. trifolii* Sym plasmid nod region of strain ANU843 (Innes et al., 1985). Insertions are indicated by vertical lines with numbers. Orientation of the β-galactosidase gene is shown for each insertion by an arrow above the number. The positions of nodA, nodB, nodC and nodD were determined from sequencing data (Rolfe et al., 1985) and by comparison to published sequences for *R. meliloti* (Egelhoff et al., 1985; Torok et al., 1984) and *R. leguminosarum* (Rosen et al. 1985). Phenotypically distinct regions I, II, III, IV and V are indicated. The direction of transcription within genes or regions is signified by the heavy arrows.

In *R. trifolii* ANU843, the genes required for host specific nodulation of clover are encoded on a 14kb HindIII fragment of the Sym plasmid (Schofield et al. (1984) Plant Mol. Biol. 3:3–11). A set of Mud-lac (MudI1734) transposon insertions into the 14kb nodulation region have been described by Innes et al., 1985. This transposon contains the *E. coli* lac operon with the upstream promoter and first two codons of the β-galactosidase lacZ gene deleted (Castihlo et al. (1984) J. Bacteriol. 158:488–495). Expression of the inserted lacZ gene is regulated by a promoter upstream or 5' to the lac operon end of the transposon. Nod-lacZ gene fusions are formed by insertion of MudI1734 into nodulation genes. Those insertions that are oriented in the direction of transcription of the gene into which they are inserted will be under the regulatory control of that nodulation gene promoter. For this reason, both the site of insertion and the orientation of insertion of the transposon in the nodulation region are important to its regulation. The location and orientation of a number of MudI1734 insertions into the *R. trifolii* nodulation region are shown in FIG. 1. For example, the insertions 121 and 218 in nodA (FIG. 1) are oriented in the direction of nodA transcription, so the gene fusions resulting from these insertions are under the control of the nodABC(IJ) promoter. In contrast, insertion 802 (FIG. 1) in nodC is oriented in the direction opposite to transcription of nodC, so expression of this nod-lac fusion will not be under the control of the nodABC(IJ) promoter.

Expression of β-galactosidase enzyme activity by nod-lac fusions reflects the regulation of the nodulation genes. β-galactosidase is readily assayed by well known methods including colorimetric assays in which chromogenic substrates such as 5-bromo-4-chloro-3-indolyl-β-D-galactoside (X-gal) or o-nitrophenyl-β-D-galactoside (ONPG) are cleaved to produce blue or yellow colored products, respectively. Studies of *R. trifolii* nodulation gene regulation using the MudI1734 insertions of FIG. 1 have demonstrated that nodD is constitutively expressed in the free-living Rhizobium, while expression of other nodulation genes including nodABCEFGHI and J is induced by stimulatory or inducing factors in legume exudates (Innes et al., 1985). Recent literature reports confirm that nodD is constitutively expressed in *R. meliloti* (Long et al. 1985) and *R. leguminosarum* (Downie et al. 1985) and that in both cases nodC is induced by legume exudates. It is further reported in these references that the nodD gene product is required in addition to a legume factor for expression of nodC and other nod genes.

Rhizobium strains, particularly *R. trifolii*, which contain Mud-lac insertions into those nodulation genes which are induced by legume exudate, for example nodA fusions, can be employed in combination with the well known assays for β-galactosidase to test substances for the ability to induce nodulation gene. Such assays are applicable to testing of plant exudates, extracts, purified fractions from exudates or extracts, as well as individual molecules prepared by purification from extracts or by synthetic methods for nodulation gene-inducing activity.

The Mud-lac insertions of FIG. 1 represent a set of recombinant DNA molecules which each contain a single Mud-lac insertion into the 14kb HindIII nodulation gene region of R. trifolii at the location noted. These recombinant DNA fragments can be inserted into recombinant vectors which are introduced into bacterial strains where the DNA of the recombinant vector is replicated resulting in the cloning of the insertion containing DNA fragments. For studies of gene regulation in R. trifolii, the 14kb HindIII fragments containing the Mud-lac insertions have been cloned into the broad host range vector pKT240 (Schofield et al., 1984; and Bagdasarian et al. (1981) Gene 16:237-247). The resultant recombinant vectors are designated pRt032 and further identified by the number of the insertion, for example pRt032:121 or pRt032:218. It is an important feature of these constructions that the 14kb nodulation region is intact except for the single insertion of the Mud11734 transposon. Any of the Mud-lac insertions in the correct orientation into the nodulation genes which are induced in response to legume exudates (nodABCEFGHIJ) should be usable in an assay for nodulation gene-inducing factors. In each of these recombinant DNA molecules or fragments, the inserted lacZ gene is under the control of a legume exudate inducible promoter and an intact nodD region, a source of nodD gene product, is provided.

Qualitative visualization of the presence of stimulatory or inducing factors in plant exudates was achieved by placing legume seedlings onto lawns of R. trifolii containing a nodA-lacZ fusion (121 or 218) which had been plated on agar in the presence of X-gal. In an alternative assay, the nodulation inducing activity of exudates was quantitatively measured by contacting liquid cultures of R. trifolii containing a nodA-lacZ fusion with seedling growth medium in the presence of ONPG. Using either or both of these methods, exudates of a variety of legume seedlings were found to induce nodA expression (Table 1). None of the exudates of non-legume seedlings that were examined (Table 1) were found to induce nodA expression. Legume exudates were confirmed to induce expression of other R. trifolii nod genes, nodABCEFGHIJ.

TABLE 1

Induction of R. trifolii nodA-lac gene fusions by various plant exudates[1]

| Source of Exudate | Method of Assay[2] | |
|---|---|---|
| | X-Gal | ONPG |
| Legumes: | | |
| White clover | + | + |
| Red clover | + | ND |
| Subterranean clover | + | + |
| Alfalfa | + | + |
| Garden pea | + | + |
| Pea var. Rondo | + | ND |

TABLE 1-continued

Induction of R. trifolii nodA-lac gene fusions by various plant exudates[1]

| Source of Exudate | Method of Assay[2] | |
|---|---|---|
| | X-Gal | ONPG |
| Afghanistan pea | + | ND |
| Soybean var. Bragg | + | + |
| Soybean var. Williams | + | + |
| Broad bean | + | + |
| French bean | + | ND |
| Lupine | + | + |
| Siratro | + | + |
| Desmodium | + | ND |
| Non-legumes: | | |
| Parasponia | − | ND |
| Corn | − | − |
| Wheat | − | − |
| Rice | − | ND |
| Bluegrass var. Kentucky | − | ND |
| Spinach | − | − |
| Cucumber | − | − |
| Brussels sprout | − | − |
| Carrot | − | − |

[1]Some of the results presented in this table appeared in Innes et al. 1985.
[2]A "+" sign indicates nod gene induction; a "−" sign indicates no induction of nod gene; "ND" indicates that the particular assay was not done. β-galactosidase assays were performed by placing plant seedlings or seedling growth medium in contact with lawns or liquid cultures of R. trifolii containing pRt032::121 or pRt032::218 in the presence of the indicated chromogenic substrate. Control strain used in these experiments was R. trifolii containing pRt032::802 which is a Mud-lac insertion in the antisense orientation in the nodC gene.

Nodulation gene-inducing factors can be isolated by aqueous ethanol extraction of legume seedlings followed by chromatography on silicic acid. Chromatographic fractions can be assayed for nodulation inducing activity as described supra. The isolation method has been described herein for extracts of white clover, but is applicable to any legume seedling. Three active fractions were isolated from white clover extract. The major constituent of each fraction was identified as a substituted flavone by conventional NMR and mass spectrometry. (See, for example, Markham and Marby (1981) The Flavonoids, Harborne et al. (eds.) Chapman and Hall, London, pp. 267-295; and Swain (1976) in *Chemistry and Biochemistry of Plant Pigments*, Vol. 2, Goodwin (ed.) Academic Press, New York, Chapter 20.) The three constituents were identified as 7,4'-dihydroxyflavone (III), 7,4'-dihydroxy-3'-methoxyflavone (also called geraldone) (VIII) and 4'-hydroxy-7-methoxyflavone (V) (see Table 2 for structures).

During the course of the isolation and identification of nodulation inducing factors in clover extracts, several other extract constituents were identified which did not have nodulation gene-inducing activity. Several of these non-active constituents, however, were found to inhibit the nod gene induction response to inducer molecules. The purification method described removes significant amounts of these materials and provides fractions that are active for induction.

TABLE 2

Induction of Nodulation Gene Expression by Flavones

| Flavone | Substitution | Nodulation Gene Induction[1] |
|---|---|---|
| I. flavone | $R_{1-10}$ = H | − |
| II. 3-hydroxyflavone | $R_1$ = OH<br>$R_{2-10}$ = H | − |
| III. 7,4'-dihydroxy-flavone | $R_4$ and $R_8$ = OH<br>$R_{1-3}$, $R_{5-7}$ and<br>$R_{9-10}$ = H | + |
| IV. 5,7-dihydroxy-flavone [chrysin] | $R_2$ and $R_4$ = OH<br>$R_1$, $R_3$, $R_{5-10}$ = H | + |
| V. 4'-hydroxy-7-methoxyflavone | $R_8$ = OH<br>$R_4$ = OMe<br>$R_{1-3}$, $R_{5-7}$, and $R_{9-10}$ = H | weak + |
| VI. 5,7,4'-trihydroxy-flavone [apigenin] | $R_2$, $R_4$ and $R_8$ = OH<br>$R_1$, $R_3$, $R_{5-7}$ and $R_{9-10}$ = H | + |
| VII. 7,4'-dihydroxy-3'-methoxy-flavone [geraldone] | $R_4$ and $R_8$ = OH<br>$R_7$ = OMe<br>$R_{1-3}$, $R_{5-6}$, $R_{9-10}$ = H | + |
| VIII. 3,5,7,4'-tetra-hydroxyflavone [kaempferol] [morin] | $R_1$, $R_2$, $R_4$ and $R_8$ = OH<br>$R_3$, $R_{5-7}$ and $R_{9-10}$ = H | +<br><br>+ |
| IX. 3,7,3',4'-tetra-hydroxydihydro-flavone [fisetin] | $R_1$, $R_4$, $R_7$ and $R_8$ = OH<br>$R_{2-3}$, $R_{5-6}$ and $R_{9-10}$ = H | − |
| X. 3,5,7,3',4',5'-hexa-hydroxyflavone | $R_1$, $R_2$, $R_4$, $R_7$, $R_8$ and $R_9$ = OH<br>$R_3$, $R_{5-6}$ and $R_{10}$ = H | − |
| XI. 7,4'-dihydroxy-flavone-8-C-glucoside [bayin] | $R_4$ and $R_8$ = OH<br>$R_5$ = C glucoside<br>$R_{1-3}$, $R_{6-7}$ and $R_{9-10}$ = H | − |
| XII. 3,5,7,3',4'-penta-hydroxy-3-O-rutinoside [rutin] | $R_2$, $R_4$, $R_7$ and $R_8$ = OH<br>$R_1$ = O-rutinoside<br>$R_3$, $R_{5-6}$ and $R_{9-10}$ = H | weak + |
| XIII. 5,3'-dihydroxy-4'-methoxy-flavone-7-O-rutinoside [diosmin] | $R_2$, $R_7$ = OH<br>$R_8$ = OMe<br>$R_1$, $R_3$, $R_{5-6}$, $R_{9-10}$ = H<br>$R_4$ = O-rutinoside | − |
| XIV. 3,5,7,3',4'-penta-hydroxydihydro-flavone [taxifolin][2] | $R_1$, $R_2$, $R_4$, $R_7$ and $R_8$ = OH<br>$R_3$, $R_{5-6}$, and $R_{9-10}$ = H | weak + |
| XV. 5,7,4'-trihydroxy-flavanone [narigenin][2] | $R_2$, $R_4$ and $R_8$ = OH<br>$R_1$, $R_3$, $R_{5-7}$, $R_{9-10}$ = H | + |
| XVI. 5,7,4'-trihydroxy-flavanone[2] 7-O-rhamnoglucoside [naringin] | $R_2$, $R_8$ = OH<br>$R_1$, $R_3$, $R_{5-7}$, $R_{9-10}$ = H<br>$R_4$ = O-rhamnoglucoside | − |

[1] A "+" sign indicates induction of nodA-lac gene fusions; a "−" sign indicates no induction of nodA-lac gene fusions; induction is assayed as β-galactosidase activity using X-gal or ONPG methods.

[2] Taxifolin, naringenin and naringin are flavanones (dihydroflavones) in which the double bond between carbons 2 and 3 of the fused ring is saturated (see structure, above).

TABLE 3

Flavone Related Molecules Displaying No Nodulation Gene-Inducing Activity

| Compound |
|---|
| Coumarin |
| Coumestrol |
| Daidzein |
| Biochanin A |
| Formononetin |
| Umbelliferone |
| Fraxin |
| o-coumaric acid |
| p-coumaric acid |
| m-coumaric acid |

Flavones as a class are distributed widely in plant tissue, usually substituted with sugar moieties at the 7 hydroxy position, but sometimes in the free (aglucon) form. Naturally-occurring flavones include both hydroxylated and methoxylated derivatives with substitutions at carbons 5,7,4' and 3' predominating. For a general description of the chemistry, biochemistry and occurrence of flavones and derivatives, see Goodwin (ed.) *Chemistry and Biochemistry of Plant Pigments* (1976) Academic Press, New York, Chapters 8, 9 and 16. The flavones apigenin, luteolin and the flavanols (3-hydroxyflavones) kaempferol, quercetin and myricetin are particularly widespread in plant tissue. In contrast, the aglucons 7,4'-dihydroxy flavone and geraldone have been reported only in legumes including *Medicago sativa*, Trifolium, Pterocarpus and Baptisia (Wong and Francis (1968) Phytochemistry 7:2123-2129; Olah and Sherwood (1971) Phytopathology 61:65-69; Maurya and Ray (1984) J. Natural Products 47:179-181; Markham and Marbry (1968) Phytochemistry 7:791-801; and Eade et al. (1966) Aust. J. Chem. 19:1717-1727).

Figure 2:
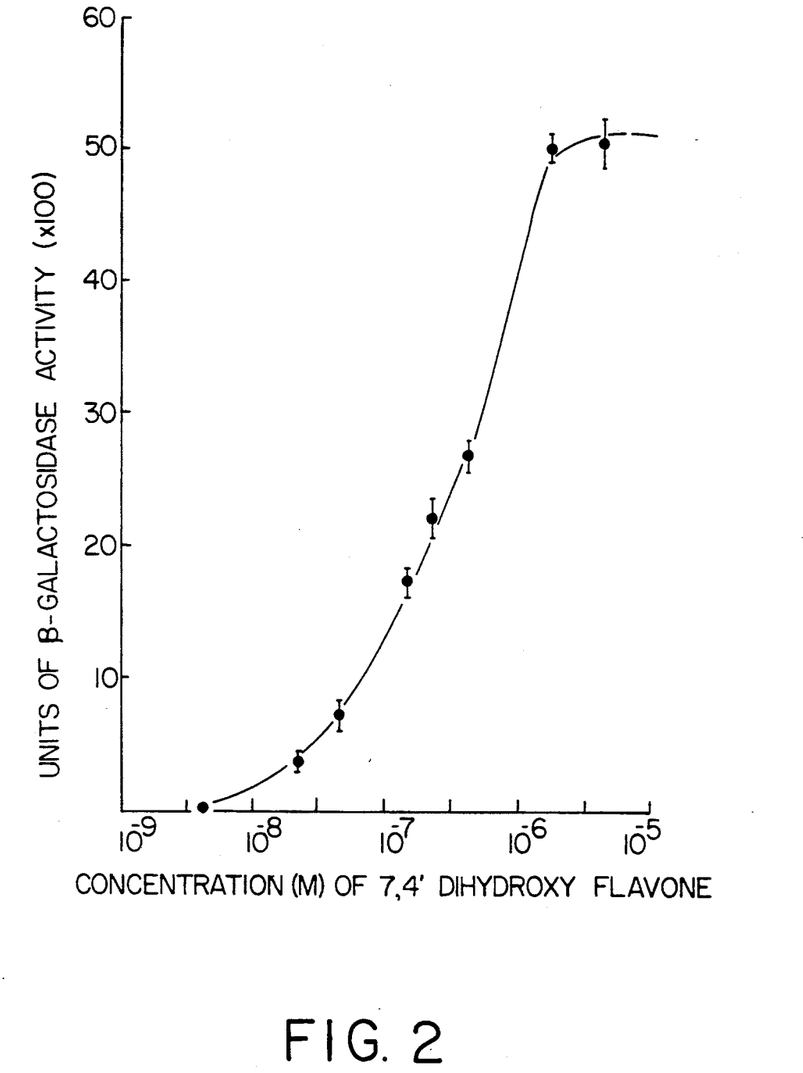
FIG. 2 is a graph showing the level of the induction of *R. trifolii* nodA gene (insertion 218) expression by 7,4'-dihydroxyflavone as assayed by β-galactosidase activity (units) (Miller (1972) *Experiments in Molecular Genetics*, Cold Spring Harbor Laboratory, New York, p. 352). Sterile solutions of 7,4' dihydroxyflavone were incubated with about $5 \times 10^8$ bacteria in a total volume of 1.60 ml for 4 hours at 29° C. A sample of this mixture (0.4 ml) was then assayed for β-galactosidase activity (absorption measured at 420 nm, Miller, 1972).

Synthetic 7,4'-dihydroxyflavone was found to have nodulation gene-inducing activity confirming its identification as an active constituent in clover exudate. The expression of nodA::lac fusions was detected (ONPG assay) at concentrations of 7,4'-dihydroxyflavone as low as about $1 \times 10^{-8}$M and expression increased strongly with increasing concentration to about $6 \times 10^{-6}$M, above which concentration the flavone is no longer soluble in aqueous solution (FIG. 2). Nod::lac gene fusions in the various nodulation genes nodABCEFGIJ were all readily induced by 7,4'-dihydroxyflavone.

The level of expression of nodA-lac fusions, measured as units of β-galactosidase activity by the ONPG assay, induced by 7,4'-dihydroxyflavone was found to be pH dependent. Expression was maximal between pH 6.8-6.9, dropped off about 3-fold by pH 8.0 and dropped off more sharply at acidic pH (100-fold by pH 5.0). The mechanism of this pH dependence is as yet unknown.

It is well known that nodule development is inhibited by fixed nitrogen, for example in the form of ammonia or nitrate (see, for example, Dazzo and Hubbell (1982) in *Nitrogen Fixation*, Vol. 2, Broughton (ed.) Clarendon Press, Oxford, pp. 274-310). Concentrations of nitrate as low as about 10-20 mM inhibit clover nodulation by *R. trifolii*. Induction of nodulation genes by the stimulator molecules of the present invention is insensitive to nitrate concentrations up to 100 mM. NodA-lac fusions in *R. trifolii* were found to remain inducible by legume exudates and 7,4'-dihydroxyflavone in the presence of concentrations of nitrate ranging from 10-100 mM.

A number of molecules structurally related to the nodulation gene-inducing flavones identified in clover exudate are available either from commercial sources or can be synthesized by published methods. For synthesis of substituted flavones in particular, see for example, Gaydou and Branchini (1978) Bull. Soc. Chim. France 2: 43-44; and Gripenberg (1962) in *The Chemistry of Flavonoid Compounds* Geussman (ed.) Pergamon Press, Oxford.

In order to define the molecular structural features that are associated with nodulation inducing activity, a number of flavones including flavanones, flavanols and dihydroflavanols, isoflavones, coumarins and related molecules were assayed for nodulation inducing activity. The results of these experiments are presented in Tables 2 and 3. Nodulation inducing activity was found to residue in a structurally identifiable group of compounds not limited to those flavones associated in particular with legumes which include specifically substituted flavones, flavonones (dihydroflavones), flavanols (3-hydroxyflavones) and dihydroflavanols. Isoflavones, including 7,4'-dihydroxyisoflavone (diadzein) an isomer of the active 7,4'-dihydroxyflavone, were found to have no activity for induction of nodulation genes. Similarly, coumarin, umbelliferone (7-hydroxycoumarin) and coumaric acid were found to have no nodulation gene stimulatory activity.

The results of Table 2 and 3 allow a designation of the structural features associated with nodulation gene-inducing activity. The absence of activity in isoflavones and coumarins indicates that the basic flavone ring structure (Table 2) common to flavones, flavanones, flavanols and dihydroflavanols is requisite for activity. Within the group of flavones, it is clear that substitution at the 7 position (see Table 2 for numbering of rings) with a hydroxyl group leads to strong stimulatory activity. It is also clear that substitution of hydroxyl or methoxyl moieties at positions 5, 3, 2' or 4' in addition to 7-hydroxyl substitution does not abolish activity. Nor, in general, does substitution of hydroxyl or methoxyl moieties at position 3' in addition to 7-hydroxyl substitution abolish activity. However, flavones or dihydroflavones substituted with either hydroxyl or methoxyl at both the 3' and 4' positions require in addition to 7-hydroxylation a hydroxyl group at the 5 position for activity. The fact that rutin, a 3-O-glycoside of the flavone quercetin, is active for nodulation gene induction not only indicates that quercetin is active but also that 3-O-glycoside substitution does not abolish inducing activity. In contrast, substitution of a glucoside at the 7 position is believed to abolish activity (i.e., dosmin and naringin, Table 2). Replacement of the 7-hydroxy group with a methoxy group decreases but does not abolish stimulatory activity as evidenced by the weak activity of 4'-hydroxy-7-methoxyflavone. By analogy to active 7-hydroxyl substituted flavones, 5-hydroxy-7-methoxyflavone, 4',5'-dihydroxy-7-methoxyflavone and 3,4',5'-trihydroxy-7-methoxyflavone and their dihydroflavone analogs are expected to have stimulatory activity, albeit weak. The fact that taxifolin and naringein, both flavanones, have stimulatory activity indicates that the double bond in the flavone fused ring (between positions 2 and 3) is not necessary for nodulation gene-inducing activity. This implies that all flavones and dihydroflavanols having substitution patterns as described above have nodulation inducing activity. Although alkoxy substituted flavone other than methoxy have not been identified from natural sources, there is no reason to believe that alternative short chain substituents like ethoxy or propoxy groups would abolish nodulation gene induction activity.

The following substituted flavones are additional examples of molecules that are indicated by the results of Table 2 to have nodulation gene-inducing activity: 7-hydroxyflavone; 7,2'-dihydroxyflavone; 5,7,4',3'-tetrahydroxyflavone (luteolin); 3,5,7,2'-tetrahydroxyflavone (datiscetin); 3,5,7,4',3'-pentahydroxyflavone (quercetin); 5,7-dihydroxy-4'-methoxyflavone (acacetin); 3,5,7-trihydroxyflavone (galangin); 3,5,7,4'-tetrahydroxyflavanone (dihydrokaempferol); 5,7,3'-tetrahydroxy-4'-methoxyflavone (diosmetin); and 3,7,4'-trihydroxyflavanone (garbanzol). The foregoing list is in no way intended to limit the scope of the invention which is defined in the appended claims.

It has been found in soybean inoculated with *Bradyrhizobium japonicum* strains USDA 110 or 138 that inoculation of one side of a split-root suppressed subsequent nodulation by the same inoculating strain on the other side of the root (Kosslak and Bohlool (1984) Plant Physiol 75: 125-130). Delayed inoculation of a second side of a soybean split root by 96 hours resulted in significant suppression of nodulation on this second side. Similar results have been found in split-root experiments of clover inoculated with *R. trifolii* ANU843, except that a 72 hour delay of inoculation was sufficient to induce suppression. The use of a single plant with a split-root for these experiments provides a control for variations in plant growth. Simultaneous inoculation of both ends of a split root with identical inocula shows no significant differences in nodulation rate. Split-root experiments can than be used to compare different inocula for delay of nodulation initiation and assess the relative competitiveness of different strains for nodulation.

Using split-root experiments, clover exudates were found to elicit earlier nodulation on clover by a nodulation delayed hybrid strain of *R. trifolii*. Table 4 presents the results of split-root experiments comparing nodulation by wild-type *R. trifolii* ANU843 and a *R. trifolii* hybrid strain containing a recombinant plasmid, designated pBRIAN which contains the nodulation and nitrogenase genes of *R. trifolii* pSym inserted into a *R. leguminosarum* pSym from which the natural nod and nif genes had been removed (Djordjevic et al. (1983) J. Bacteriol. 156: 1035-1045). The recombinant plasmid pBRIAN is a composite Sym plasmid containing *R. trifolii* nod and nif functions in a *R. leguminosarum* plasmid genetic background.

As shown in Table 4, ANU845 (pBRIAN) displays about a 3-4 day delay in nodulation in split-root experiments with wild-type ANU843. The two strains ANU843 and ANU845 (pBRIAN) were applied to the opposite sides of a clover split-root at the same time, so the observed delay in nodulation reflects delay in nodulation initiation by the hybrid strain. Table 4 also presents the results of a similar experiment in which the delayed hybrid strain is pretreated with clover exudate prior to inoculation. The delay in nodulation initiation by ANU845 (pBRIAN) is eliminated by pretreatment with exudate. In split-root experiments, strains were pretreated about 4 hours prior to inoculation. This preincubation time was chosen for convenience.

TABLE 4

Clover Split-Root Experiment: Pretreatment of Root Nodulation-Delay *R. trifolii* with Clover Extract

| Strains[1] Side of Root Inoculation | | Days after Inoculation | Percent of Plants Nodulated on | |
|---|---|---|---|---|
| A | B | | Side A | Side B |
| ANU843 | — | 6 | 60 | — |
|  | — | 10 | 83 | — |
|  | — | 12 | 100 | — |
| ANU845 (pBRIAN) | — | 6 | 40 | — |
|  | — | 10 | 71 | — |
|  | — | 12 | 87 | — |
|  | — | 14 | 100 | — |
|  | + water (control)[2] | | | |
| ANU843 | ANU845 (pBRIAN) | 6 | 6 | 6 |
|  |  | 10 |  | 60 |
|  |  | 12 |  | 80 |
|  |  | 14 |  | 100 |
|  | + clover root[2] | | | |
| ANU843 | ANU845 (pBRIAN) | 6 |  | 50 |
|  |  | 10 |  | 80 |

TABLE 4-continued

Clover Split-Root Experiment: Pretreatment of Root Nodulation-Delay *R. trifolii* with Clover Extract

| Strains[1] Side of Root Inoculation | | Days after Inoculation | Percent of Plants Nodulated on | |
|---|---|---|---|---|
| A | B | | Side A | Side B |
|  |  | 12 |  | 100 |

[1]ANU843 is a wild-type *R. trifolii*; ANU845 (pBRIAN) is a *R. trifolii* hybrid strain described in Djordjevic et al. (1983) J. Bacteriol. 156:1035-1045.
[2]In these experiments, ANU845 (pBRIAN) was preincubated in water (control) or clover root exudate for 4 hours.

Similar experiments were performed with synthetic 7,4'-dihydroxyflavone, which was identified herein as a nodulation gene stimulator. The results of these split-root experiments are shown in Table 5. Pretreatment of the wild-type ANU843 with 7,4'-dihydroxyflavone elicits a faster rate of nodulation in comparison to untreated ANU843. A similar result was observed for ANU845 (pBRIAN). These results imply that exudates, active extracts, active fractions of extracts and molecules which have nodulation gene inducing-activity will also elicit faster initiation of nodulation by certain Rhizobium strains.

TABLE 5

Clover Split-Root Experiment: Effect of Pretreatment with 7,4'-dihydroxyflavone on Nodulation Initiation Rate by *R. trifolii* Strains

| Strains[1] Side of Root Inoculation | | Days after Inoculation | Percent of Plants Nodulated on | |
|---|---|---|---|---|
| A | B | | Side A | Side B |
| Pretreat with[2] 7,4'-dihydroxy-flavone | No pretreatment | | | |
| ANU843 | ANU843 | 4 | 83 | 17 |
|  |  | 5 | 100 | 33 |
|  |  | 6 | 100 | 50 |
|  |  | 10 | 100 | 83 |
| ANU845 (pBRIAN) | ANU845 (pBRIAN) | 4 | 80 | 0 |
|  |  | 5 | 100 | 0 |
|  |  | 6 | 100 | 0 |
|  |  | 8 | 100 | 60 |
|  |  | 10 | 100 | 80 |

[1]ANU843 is a wild-type *R. trifolii*; ANU845 (pBRIAN) is a *R. trifolii* hybrid strain whose construction is described in Djordjevic et al. (1983) J. Bacteriol. 156:1034-1045.
[2]Strains were pretreated for 4 hours in $2.5 \times 10^{-6}$ M 7,4'-dihydroxyflavone (see text).

A primary use of the substituted flavones and active fractions of legume exudate of the present invention is in the inoculation of legumes to effect early initiation of nodulation and thereby enhance the competitiveness of the inoculant strain with respect to the indigenous soil rhizobia population. An inoculating composition can be prepared by combining an effective amount of a nodulation gene stimulator of the present invention with a selected strain that is capable of nodulating the legume. Alternatively, a nodulation inducing composition containing an effective amount of a nodulation gene-inducing factor in a suitable concentration of a carrier can be applied to or in the vicinity of an inoculated seed prior to, simultaneously with, or after sowing of the seed. The amount of a particular nodulation gene-inducing factor that is effective can be determined empirically by varying the concentration in the split-root experiments or by determining the concentration range over which the compound is effective for nodulation gene induction using the β-galactosidase based assays of Examples 1 and 2. Certain substituted flavones of the present invention were found to be effective for nodulation gene induction over the range of concentrations about $1 \times 10^{-8}$M to their solubility limit in water.

Direct or indirect methods of legume inoculation can be employed. During direct inoculation the bacterium is applied directly to the seed prior to sowing. This can most simply be accomplished by spraying the seed with or dipping the seed into a liquid culture containing a desired Rhizobium strain and a nodulation gene inducer. A preferred method of direct inoculation is pelleting of the seed with an inoculating composition containing a Rhizobium strain and a nodulation gene-inducing factor. Generally, the bacterium is applied to a carrier material and a pellet is formed with the carrier surrounding the seed. Many diverse carriers are known in the art and include, among others, peat, soil, calcium carbonate, dolomite, gypsum, clay minerals, phosphates, titanium dioxide, humus and activated charcoal. Any agriculturally suitable material can be employed. An adhesive material is often included in such a pellet to insure that the carrier remains in contact with the seed. Again, many acceptable adhesives are known including, among others, synthetic glues, vegetable glues, gelatin and sugars. In general, the carrier and any adhesive used are chosen to insure viability of the inoculant strain and retention of activity of nodulation gene-inducing factor. Pelleted inoculated seed containing an inducing factor can be directly sown into the field. Alternatively, a conventionally prepared inoculated seed or seed pellet containing the desired strain can be contacted with an inducing composition containing an effective amount of a nodulation gene inducer before, with or after sowing of the inoculated seed.

During indirect inoculation an inoculating composition of the present invention containing an inoculant strain and an effective concentration of a nodulation gene inducer is introduced in the vicinity of the seed at the time of sowing. The inoculating composition is in a suitable carrier material to aid in application. The carrier can be a solid or liquid material but must be non-toxic to plant and bacteria, as well as chemically inert to nod gene inducers. Examples of carriers include, among others, aqueous solutions with or without buffering agents; peat and other materials cited above as potential carriers. Bacterial nutrients may also be included in such carriers.

The following references provide a description of basic techniques in the art of agricultural inoculation: Brockwell (1962) Aust. J. Agr. Res. 13: 638; Bergersen et al. (1958) J. Aust. Inst. Agric. Sci. 24: 158; Hastings et al. (1962) N.Z. J. Agr. 104: 330; Fraser (1966) J. App. Bacteriol. 29: 587; Schiel et al. (1970) Rev. Invest. Agropec. Ser. 2 7: 239; Iswaran et al. (1971) Zentralbl. Bakteriol. Parasitenk. Infektionskr. Abt. II 126: 43,45.

Another use of the nodulation gene-inducing factors of the present invention is for selective induction in bacteria of genes containing a legume exudate-inducible promoter and a structural gene under its control. Expression of a gene containing a legume-inducible promoter, for example the nodABC(IJ) promoter of *R. trifolii*, can be activated by addition of an effective amount of a nodulation gene inducer to a culture of bacteria which contains the gene and in which the legume-inducible promoter is active. Legume-inducible promoters are active (i.e., respond to nodulation gene inducers) in strains of Rhizobium, Bradyrhizobium and Agrobacterium. Specifically, activity of the *R. trifolii* nodA promoter has been demonstrated in *R. meliloti*, fast-growing cowpea Rhizobium strain NGR 234, and *Agrobacterium tumefaciens*. The broad host range plasmid pRt032:121 which contains a MudI1734 insertion into the nodA gene of the 14 kb nodulation region of *R. trifolii* was transferred into these strains after which activity of the promoter was shown by $\beta$-galactosidase expression in response to legume exudate or nodulation gene-inducing factors. Bradyrhizobium strains have been shown to contain nod gene promoters containing sequences associated with legume-inducible expression.

Expression of genes which contain legume inducible promoters including heterologous or chimeric genes and nod-gene fusions can be selectively controlled by nodulation inducing factors. Nod-gene fusions are prepared by insertion of a structural gene into a nodulation gene as exemplified by the Mud-lac gene fusions in *R. trifolii* (Innes et al. 1985). Legume exudate inducible chimeric genes are prepared by joining or ligating a heterologous structural gene to a nodulation gene promoter. As is well known in the art, the heterologous gene must be inserted or ligated in the correct orientation (vide infra) with respect to the promoter to be placed under its regulatory control.

In principle, any commercially useful gene product originating from either prokaryotic or eukaryotic genes can be selectively expressed by addition of a nodulation gene-inducing factor. Limitations well known in the art include gene products that are toxic to the production bacterium. For eukaryotic genes, no introns must be present in the gene coding region; if introns are present in the chromosomal gene, a cDNA copy of the structural gene can be employed in constructions. Structural gene products whose expression can be controlled using this method include, among others, *Bacillus thuringiensis* insect toxin, the sweet plant protein thaumatin and metallothienein (Karin, M. and R. I. Richards (1982) Nucleic Acids Res. 10: 3165; Wong et al. (1983) J. Biol. Chem. 258: 160; Edens et al. (1982) Gene 18: 1-12). An important aspect of the method is that a source of nodD gene product must be present, in addition to a nodulation gene-inducing factor, in order to activate legume exudate-inducible promoters. The bacterium must contain the nodD gene in a form that is expressible. *R. trifolii* Mud-lac fusions into the legume-inducible nod genes are examples of DNA constructions which meet this requirement. Alternatively, it may be possible to supply nodD gene product.

Those of ordinary skill in the art will appreciate that the invention described herein and the method of isolation and assay methods specifically described are susceptible to variations and modifications other than as specifically described. It is to be understood that the invention includes all such variations and modifications which fall within its spirit and scope. The following examples are provided for illustrative purpose only and are not intended to limit the scope of the invention.

EXAMPLE 1

Nodulation Gene-Inducing Factor Assay, Method 1

Stimulation of nod gene expression was assayed by measuring $\beta$-galactosidase activity expressed by strains of *R. trifolii* containing appropriate nod gene-Mud-lac fusions (FIG. 1), created by insertion of the transposon MudI1734. In a qualitative assay, employing the chromogenic substrate 5-bromo-4-chloro-3-indolyl-$\beta$-D-galactoside (X-gal), *R. trifolii* (0.3 ml) of a mid-log phase culture, about $1 \times 10^8$ bacteria/ml, were added to soft agar overlays of nitrogen-free Fahraeus medium spread over Fahraeus medium agar plates (Rolfe et al. (1980) Plant Science Lett. 19: 277–284; J. M. Vincent (1970) *A Manual for the Practical Study of Root-Nodule Bacteria*, I.B.P. Handbook No. 15, Blackwell, Oxford and Edinburgh). The substrate X-gal was incorporated into the medium at 4 mg/ml. After solidification of the agar overlay, the substance to be tested for nodulation gene-inducing activity was placed in contact with the surface of the agar overlay. The plates were incubated at 29° C. in the dark for 18 hours to allow development of a bacterial lawn after which the lawn was examined for production of blue coloration at the site of contact with the test substance. The presence of blue coloration indicated induction of $\beta$-galactosidase and stimulation of nod gene expression. For many of the assays performed, the Mud-lac insertion 121 carried in plasmid pRt032, pRt032(::121), was employed. This plasmid was introduced into a Sym plasmid cured strain of *R. trifolii* ANU845 designated ANU845(pRt032::121) which was then used as the assay strain. This strain *R. trifolii* ANU845(pRt032::121) has been placed on deposit with the Northern Regional Research Center, 1815 North University Street, Peoria, Ill., 61604, on Mar. 24, 1986, Accession Number B-18063. An alternative assay strain is *R. trifolii* ANU845 (pRt032::218). Plasmids carrying antisense Mud-lac fusion are useful in negative control experiments. This method can be used to assay plant exudates (Table 1), extracts, purified fractions (Example 3) and individual molecules (Tables 2,3) for activity. The test substance can be placed in contact with the bacterial lawn in a variety of ways, for example by contacting seedling roots with the agar surface or by placing filter paper impregnated with the test substance on the agar surface.

EXAMPLE 2

Nodulation Inducing Factor Assay, Method II

A second quantitative assay method employing the *R. trifolii* nod gene regulation assay strains containing Mud-lac fusions was used to measure induction of nodulation gene expression. This method employed liquid cultures of the assay bacterium with ONPG as the chromogenic substrate for $\beta$-galactosidase. The assay was performed essentially as described by Miller (1972) *Experiments in Molecular Genetics*, Cold Spring Harbor Laboratory, New York, p. 352.

A culture of *R. trifolii* containing a nodA::lac fusion (pRt032::121 or pRt032::218) was grown to early or mid-logarithmic phase in BMM medium (Rolfe et al., 1980) or TM minimal medium (Innes et al., 1985). Samples of the liquid bacterial culture containing about $5 \times 10^8$ bacteria were added to an induction medium (total volume 1.6 ml) of BMM containing nodulation inducing factor. Controls were similarly prepared by adding culture to a control medium with no nodulation inducing factor present. After an incubation period of about 4 hours the treated and control samples were assayed for $\beta$-galactosidase activity. The 4 hour incubation period was chosen for convenience. Induction of the nod-lac fusions was observed as early as 30 minutes after addition of the inducer.

ONPG assays with plant exudates were performed as in Innes et al., 1985. For example, clover seeds were sterilized and germinated as described in Rolfe et al., 1980. Day old sprouts (about 10) were transferred to 25 mm diameter glass test tubes containing a stainless steel screen (18 mesh) supported above 10 ml of TM or BMM medium. The tubes with seedlings were then subjected to the same temperature and light regime used in plate assays. The clovers were allowed to grown down into the medium for 4 days. This seedling growth medium was used to assess induction by clover-exudate. Similarly prepared exudates were used in split-root experiments (Example 4). Preparations of active exudates did not require pre-treatment or contact of the clover with rhizobia.

Samples (0.4 ml) for assay were added to an equal amount (0.4 ml) of Z-buffer (60 mM $Na_2HPO_4$, 40 mM $NaH_2PO_4$, 10 mM KCl, 1 mM $MgSO_4$ and 50 mM $\beta$-mercaptoethanol, pH 7.0). The bacterial cells were ruptured by addition of chloroform (2 drops/0.8 ml sample) and 0.1% (w/v) sodium dodecylsulfate (SDS) (1 drop/0.8 ml) followed by thorough vortexing. The assay mixtures were then incubated at 42° C. for 30 minutes. After this incubation, the chromogenic substrate ONPG was added (0.67 mg/ml). After development of the yellow color, the reaction was stopped by addition of 0.4 ml of 1M $Na_2CO_3$ to each assay tube. The same amount of color development time was allowed for all samples in an individual experiment. Cell debris was precipitated by centrifugation and the absorbence of the cleared samples were measured at 420 nm. FIG. 2 presents the results of an ONPG assay using *R. trifolii* (pRt032::218) to follow nodA gene induction as a function of the concentration of 7,4'-dihydroxyflavone added.

EXAMPLE 3

Isolation and Identification of Nodulation Inducing Factors

Nodulation inducing factors can be isolated from legume seedlings by extraction with aqueous ethanol followed by separation of active fractions using chromatography (column or thin layer) on silicic acid. Activity of separated fractions can be assayed using the methods of example 1 or 2. The isolation method is described herein for white clover seedlings but is applicable to seedlings of other legumes.

White clover seed was immersed in 70% ethanol for 15 minutes followed by thorough washing with distilled water. The seed was then sterilized with 3% sodium hypochlorite for 15 minutes, irrigated with sterile distilled water until the washings were clear and dispensed into fifty sterile petri dishes. Sterile water (10 ml) was added to each dish and the seed stored overnight for germination at 4° C. The dishes were then drained, washed thoroughly with sterile distilled water and the germinated seeds were axenically grown in a humid atmosphere in the dark for 48 hours. The resulting clover seedlings were extracted for 4 hours with 200 ml of 40% (v/v) ethanol/$H_2O$. The extract was coarse filtered through cheesecloth after which the filtrate was diluted with 800 ml of absolute ethanol in order to precipitate proteins. The mixture was allowed to stand overnight in the refrigerator, after which the protein precipitate was removed. The supernatant was evaporated under reduced pressure at less than or equal to 40° C. and the residue dried. Water was removed by repeated evaporations of added ethanol resulting in a dried cake of residue.

The dried residue cake was stirred in 200 ml of methanol for 6 hours until the cake had broken up. Chloroform (400 ml) was added with swirling to precipitate polar components. The mixture was filtered and the solvents were removed from the filtrate under reduced pressure. The residue was applied to a chromatographic column containing silicic acid (Kieselgel 60, Merck) and fractions were eluted with a solution of chloroform/methanol (v/v) 90:10. Elution was continued until a prominent yellow band (unidentified) had almost reached the bottom of the column. Thin layer chromatography on silicic acid (Kieselgel 60 Alufolien, Merck) using chloroform/methanol (v/v) 96:4 indicated that all of the fluorescent material associated with nodulation inducing activity had been eluted from the column at this point. The eluted fractions were combined and the solvents were removed by evaporation. The temperature of the material was kept at 40° C. or less during solvent evaporation. It was found to be preferable to remove a nonactive contaminant, formononetin, at this stage of the isolation by repeated crystalization from ethanol. After removal of formononetin, the mother liquors were combined and ethanol removed by evaporation. The resulting residue was redissolved in 0.5 ml of chloroform/methanol v/v 96:4 and rechromatographed on silicic acid eluting with the same solvent. The course of the separation was followed by viewing fluorescent bands associated with flavones and activity on the column under ultraviolet light. Three active fractions were isolated, designated A, B, and C in order of increasing mobility on silicic acid. The major constituents of fractions A, B and C were identified as 7,4' dihydroxyflavone, 7,4' dihydroxy-3'-methoxyflavone and 4'-hydroxy-7-methoxyflavone by conventional NMR and mass spectrometry techniques.

Fraction A had identical spectroscopic (UV, NMR) and chromatographic (paper, tlc) properties to synthetic 7,4'-dihydroxyflavone. Fraction B had the same chromatographic properties as previously reported for geraldone (Wong et al. (1965) Phytochem. 4: 89–95) and an NMR spectrum consistent with the proposed structure. Fraction C had an NMR characteristic of a flavone (singlet at 6.72 ppm) (Markham and Mabry, 1981) with a methoxy singlet (3.97 ppm) consistent with 4'-hydroxy-7-methoxyflavone. The mass spectrum of C contained a parent, molecular mass peak at 268 again consistent with the identification. All three fractions exhibited strong blue fluorescence, modified by exposure to ammonia, that is characteristic of flavones having no 5-substituent (Markham and Mabry, 1981).

EXAMPLE 4

Split-Root Experiment

Split-root experiments were performed using a modification of an agar plate screening method for clover nodulation (Rolfe et al. (1980) Plant Science Lett. 19: 277–284). Certified commercial seed of subterranean clover (*Trifolium subterraneum*) was employed in these experiments. Clover seeds were sterilized by placing them in concentrated sulfuric acid for 3 minutes. The seeds were then washed thoroughly in distilled water and subjected to 13% (w/v) aqueous sodium hypochlorite for 60 minutes. After a second thorough water washing, the seeds were placed on Bergersen's modified medium (BMM, Bergersen (1961) Aust. J. Biol. Sci. 14: 349) for overnight germination at 28° C. Freshly germinated plants were gently squeezed at the root tip with fine forceps to create a split root. This technique yields better results than cutting or slicing of the root tip.

Split-root plants were then placed in a growth cabinet for 2–3 days to allow lateral root growth (temperature). Individual plants were then transferred to agar plates containing modified Fahreus medium (Rolfe et al., 1980 and Vincent, 1970). During preparation of the agar plates, plastic dividers were inserted into the agar. Insertion of the dividers provided a wedge shaped region in the agar. Plants were placed on the plates so that two sides of the split root were positioned one on either side of the wedge shaped region so that cross contamination between inocula was minimized and to ensure that the roots remained separated during the course of the experiments. Plants were allowed to settle and attach to the agar about 24 hours before inoculation. Split roots were then inoculated, for example by direct application of the bacterial culture to the root surface or by inoculating a patch of agar over which the root would grow.

The *R. trifolii* strain used as an inoculant (ANU843, or ANU845 (pBRIAN)) was pregrown in BMM at 29° C. This medium employs mannitol as a carbon source. The use of other carbon sources such as glucose or lactose may affect nodulation gene induction. Cultures in early or mid-logarithmic growth phase were employed for inocula. Cells were pretreated with clover plant exudate by addition of exudate (3.0 ml) to 1 ml of culture. Alternatively, cells were pretreated with nodulation gene inducers, for example 7,4' dihydroxyflavone, by addition of an effective amount of the compound to cells. In the case of 7,4' dihydroxyflavone the preincubation concentration used was $2.5 \times 10^{-6}$ M.

To compare the rate of nodule initiation of two different inocula containing different strains or pretreated and non-pretreated strains, the inocula are applied one to either side of the split-root. After inoculation, the agar plates were sealed. Adequate aeration was provided by slits in the film used to seal the plates. Plates were then incubated vertically in a growth cabinet with a 22° C., 18-hour day, 18° C. 6-hour night cycle employing light intensity of 400–500 $\mu EM^{-2}s^{-1}$. Typically 100 individual plants are used for each comparison. Plant roots are examined at intervals (typically daily) and scored for nodulation. Results (Table 4, 5) are reported as the percent of split-roots nodulated as a function of time after inoculation.

We claim:

1. A composition for inoculating a legume, which composition consists essentially of:
   (a) a bacterium of the genus Rhizobium, which bacterium nodulates said legume, and
   (b) an amount of a Rhizobium nodulation gene-inducing factor effective for induction of a nodA gene of *Rhizobium trifolii*, wherein said nodulation gene-inducing factor is a substituted flavone selected from the group consisting of a flavone and a flavanone, having the molecular structure:

wherein the bond between $C_2$ and $C_3$ is either a single or a double bond and wherein:
$R_1$ is H, OH, OMe or O-glycoside;

$R_2$ is H, OH or OMe, except that $R_2$ is OH when both $R_7$ and $R_8$ are OH or OMe;

$R_3$ is H;

$R_4$ is OH or OMe, except that $R_4$ is OMe only when $R_8$ is OH, $R_2$ is OH, $R_8$ and $R_2$ are both OH or $R_8$, $R_2$ and $R_1$ are all OH and all other substituents are H;

$R_5$ is H;

$R_6$ is H;

$R_7$ is H, OH or OMe;

$R_8$ is H, OH or OMe;

$R_9$ is H; and $R_{10}$ is H;

except that said nodulation gene-inducing factor is not quercetin or rutin.

2. The composition of claim 1 wherein $R_1$ is H.
3. The composition of claim 1 wherein $R_1$ is OH.
4. The composition of claim 1 wherein $R_4$ is OH.
5. The composition of claim 1 wherein $R_7$ is H.
6. The composition of claim 1 wherein $R_8$ is OH.
7. The composition according to claim 1 wherein said bacterium of the genus Rhizobium is a strain of *Rhizobium trifolii*.
8. The composition of claim 1 wherein $R_1$ is H, $R_2$ is H or OH, and $R_4$ is OH.
9. The composition of claim 1 wherein $R_1$ is H, $R_4$ is OH and $R_7$ and $R_8$ are either both H or both OH.
10. A method of inoculating a legume with a culture of a strain of the genus Rhizobium, the bacteria of which culture nodulate the roots of said legume, which method comprises the steps of:

(a) combining said culture of a strain of the genus Rhizobium with an amount of a composition consisting essentially of a Rhizobium nodulation gene-inducing factor effective for induction of a nodA gene of *Rhizobium trifolii* wherein said nodulation gene-inducing factor is a substituted flavone selected from the group consisting of a flavone and a flavanone having the molecular structure:

wherein the bond between $C_2$ and $C_3$ is either a single or a double bond and wherein:

$R_1$ is H, OH, OMe or O-glycoside;

$R_2$ is H, OH or OMe, except that $R_2$ is OH when both $R_7$ and $R_8$ are OH or OMe;

$R_3$ is H;

$R_4$ is OH or OMe, except that $R_4$ is OMe only when $R_8$ is OH, $R_2$ is OH, $R_8$ and $R_2$ are both OH or $R_8$, $R_2$ and $R_1$ are all OH and all other substituents are H;

$R_5$ is H;

$R_6$ is H;

$R_7$ is H, OH or OMe;

$R_8$ is H, OH or OMe;

$R_9$ is H; and $R_{10}$ is H; and wherein said nodulation gene-inducing factor is not quercetin or rutin; and (b) inoculating said legume with said culture of a strain of the genus Rhizobium combined with said nodulation gene-inducing factor.

11. The method according to claim 10 wherein $R_1$ is H.
12. The method according to claim 10 wherein $R_1$ is OH.
13. The method according to claim 10 wherein $R_4$ is OH.
14. The method according to claim 10 wherein $R_7$ is H.
15. The method according to claim 10 wherein $R_8$ is OH.
16. The method according to claim 10 wherein said strain of the genus Rhizobium is *R. trifolii*.
17. The method according to claim 10 wherein $R_1$ is H, $R_2$ is H or OH, and $R_4$ is OH.
18. The method according to claim 10 wherein $R_1$ is H, $R_4$ is OH and $R_7$ and $R_8$ are either both H or both OH.
19. A method of inoculating a legume with a culture of a strain of the genus Rhizobium, the bacteria of which culture nodulate the roots of said legume, which method comprises the steps of (a) inoculating a seed of said legume with said culture of a strain of the genus Rhizobium; and (b) applying in the vicinity of said seed a nodulation inducing composition comprising an amount of a Rhizobium nodulation gene-inducing factor effective for induction of a nodA gene of a *Rhizobium trifolii*, which factor comprises a substituted flavone wherein said substituted flavone is selected from the group consisting of a flavone and a flavanone having the molecular structure:

wherein the bond between $C_2$ and $C_3$ is either a single or a double bond and wherein:

$R_1$ is H, OH, OMe or O-glycoside;

$R_2$ is H, OH or OMe, except that $R_2$ is OH when both $R_7$ and $R_8$ are OH or OMe;

$R_3$ is H;

$R_4$ is OH or OMe, except that $R_4$ is OMe only when $R_8$ is OH, $R_2$ is OH, $R_8$ and $R_2$ are both OH or $R_8$, $R_2$ and $R_1$ are all OH and all other substituents are H;

$R_5$ is H;

$R_6$ is H;

$R_7$ is H, OH or OMe;

$R_8$ is H, OH or OMe;

$R_9$ is H; and $R_{10}$ is H; and wherein said nodulation gene-inducing factor is not quercetin or rutin.

20. The method of claim 19 wherein said culture of a strain of the genus Rhizobium is selected from the group consisting of *R. trifolii, R. meliloti, R. leguminosarum,* and cowpea *Rhizobium sp.*

21. The method according to claim 19 wherein $R_1$ is H.

22. The method according to claim 19 wherein $R_1$ is OH.

23. The method according to claim 19 wherein $R_4$ is OH.

24. The method according to claim 19 wherein $R_7$ is H.

25. The method according to claim 19 wherein $R_8$ is OH.

26. The method of claim 19 wherein said strain of the genus Rhizobium is *R. trifolii.*

27. The method according to claim 19 wherein $R_1$ is H, $R_2$ is H or OH, and $R_4$ is OH.

28. The method according to claim 19 wherein $R_1$ is H, $R_4$ is OH and $R_7$ and $R_8$ are either both H or both OH.

29. A composition for inoculating a legume, which composition consists essentially of:
   (a) a bacterium of the genus Rhizobium, which bacterium nodulates said legume, and
   (b) an amount of a Rhizobium nodulation gene-inducing factor effective for induction of a nodA gene of *Rhizobium trifolii,* wherein said nodulation gene-inducing factor is a substituted flavone selected from the group consisting of 4',7-dihydroxyflavone, 5,7-dihydroxyflavone, 4',5,7-trihydroxyflavone, 4',7-dihydroxy-3'-methoxyflavone, 4'-hydroxy-7-methoxyflavone, 3,4',5,7-tetrahydroxyflavone, 4',5,7-trihydroxyflavanone and 3,3',4',5,7-pentahydroxyflavanone.

30. The composition of claim 29 wherein said flavone is selected from the group consisting of 4',7-dihydroxyflavone, 5,7-dihydroxyflavone, 4',7-dihydroxy-3'-methoxyflavone, and 4'-hydroxy-7-methoxyflavone.

31. The composition of claim 29 wherein said flavone is selected from the group consisting of 4',7-dihydroxyflavone, 4',7-dihydroxy-3'-methoxyflavone, and 4'-hydroxy-7-methoxyflavone.

32. The composition of claim 29 wherein said bacterium is a strain of *Rhizobium trifolii.*

33. A method for inoculating a legume with a culture of a strain of the genus Rhizobium, the bacteria of which culture nodulate the roots of said legume, which method comprises the steps of
   (a) inoculating a seed of said legume with said culture of a strain of the genus Rhizobium; and
   (b) applying in the vicinity of said seed of said legume a nodulation inducing composition comprising an amount of a Rhizobium nodulation gene-inducing composition comprising an amount of a Rhizobium nodulation gene-inducing factor effective for induction of a nodA gene of a *Rhizobium trifolii,* which factor comprises a substituted flavone selected from the group consisting of 4',7-dihydroxyflavone, 5,7-dihydroxyflavone, 4',5,7-trihydroxyflavone, 4',7-dihydroxy-3'-methoxyflavone, 4'-hydroxy-7-methoxyflavone, 3,4',5,7-tetrahydroxyflavone, 4',5,7-trihydroxyflavanone and 3,3',4',5,7-pentahydroxyflavanone.

34. The method according to claim 33 wherein said flavone is selected form the group consisting of 4',7-dihydroxyflavone, 5,7-dihydroxyflavone, 4',7-dihydroxy-3'-methoxyflavone, and 4'-hydroxy-7-methoxyflavone.

35. The method according to claim 33 wherein said flavone is selected form the group consisting of 4',7-dihydroxyflavone, 4',7-dihydroxy-3'-methoxyflavone, and 4'-hydroxy-7-methoxyflavone.

36. The method according to claim 33 wherein said strain is a strain of *Rhizobium trifolii.*

37. A method of inoculating a legume with a culture of a strain of the genus Rhizobium, the bacteria of which culture nodulate the roots of said legume, which method comprises the steps of:
   (a) combining said culture of a strain of the genus Rhizobium with an amount of a composition consisting essentially of a Rhizobium nodulation gene-inducing factor effective for induction of a nodA gene of *Rhizobium trifolii* wherein said nodulation gene-inducing factor is a substituted flavone selected from the group consisting of 4',7-dihydroxyflavone, 5,7-dihydroxyflavone, 4',5,7-trihydroxyflavone, 4',7-dihydroxy-3'-methoxyflavone, 4'-hydroxy-7-methoxyflavone, 3,4',5,7-tetrahydroxyflavone, 4',5,7-trihydroxyflavanone and 3,3',4',5,7-pentahydroxyflavanone and
   (b) inoculating said legume with said culture of a strain of the genus Rhizobium combined with said nodulation gene-inducing factor.

38. The method of claim 37 wherein said flavone is selected from the group consisting of 4',7-dihydroxyflavone, 5,7-dihydroxyflavone, 4',7-dihydroxy-3'-methoxyflavone, and 4'-hydroxy-7-methoxyflavone.

39. The method of claim 37 wherein said flavone is selected from the group consisting of 4',7-dihydroxyflavone, 4',7-dihydroxy-3'methoxyflavone, and 4'-hydroxy-7-methoxyflavone.

40. The method of claim 37 wherein said strain is a strain of *Rhizobium trifolii.*

* * * * *